United States Patent
Parvatiyar et al.

(10) Patent No.: US 10,301,232 B2
(45) Date of Patent: May 28, 2019

(54) PROPELLANT AND SELF-PROTECTION COMPOSITIONS

(71) Applicant: HONEYWELL INTERNATIONAL INC., Morristown, NJ (US)

(72) Inventors: Madan Parvatiyar, Williamsville, NY (US); Barbara Ruth Decaire, Lancaster, NY (US); Ryan Hulse, Getzville, NY (US); Anthony Anzalone, Angola, NY (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 109 days.

(21) Appl. No.: 15/663,620

(22) Filed: Jul. 28, 2017

(65) Prior Publication Data

US 2018/0029953 A1 Feb. 1, 2018

Related U.S. Application Data

(63) Continuation of application No. PCT/US2017/044526, filed on Jul. 28, 2017.

(60) Provisional application No. 62/368,013, filed on Jul. 28, 2016.

(51) Int. Cl.
```
C06D 7/00      (2006.01)
C09K 3/30      (2006.01)
A61K 36/81     (2006.01)
F41H 9/10      (2006.01)
```

(52) U.S. Cl.
CPC ............ *C06D 7/00* (2013.01); *A61K 36/81* (2013.01); *C09K 3/30* (2013.01); *F41H 9/10* (2013.01)

(58) Field of Classification Search
None
See application file for complete search history.

(56) References Cited

U.S. PATENT DOCUMENTS

| | | | |
|---|---|---|---|
| 5,281,450 A † | 1/1994 | Yaniv | |
| 5,821,450 A * | 10/1998 | Fedida | C06D 7/00 102/370 |
| 8,734,671 B2 * | 5/2014 | Hulse | A01N 25/06 252/67 |

OTHER PUBLICATIONS

PCT Application No. PCT/US2017/044526—PCT Search Report and Written Opinion dated and published Oct. 16, 2017.†

\* cited by examiner
† cited by third party

*Primary Examiner* — Nannette Holloman
(74) *Attorney, Agent, or Firm* — Colleen D. Szuch

(57) ABSTRACT

Disclosed is a pepper spray composition comprising: (a) a chemical irritant; (b) a propellant, wherein the propellant comprises transHFO-1234ze; (c) a solvent, wherein said solvent comprises transHFO-1233zd; and (d) a non-ionic surfactant and/or an ionic surfactant.

23 Claims, No Drawings

PROPELLANT AND SELF-PROTECTION COMPOSITIONS

CROSS REFERENCE TO RELATED APPLICATIONS

The present invention is related to as a continuation of PCT Application No. PCT/US17/44526, filed Jul. 28, 2017, which is incorporated herein by reference. The present invention also claims the priority benefit of U.S. Provisional Application No. 62/368,013, filed Jul. 28, 2016, which is incorporated herein by reference.

FIELD

The present invention is directed to spray formulations for repelling and/or temporarily incapacitating a target. The formulations comprise a pepper extract and a propellant with a compatibilizer system. The invention further relates to a non-toxic, non-flammable and environmentally friendly propellant/compatibilizer system for use in pepper sprays for self-protection that is useful over a wide range of operating conditions and particularly suitable for use in an aerosol spray and allows a highly stable spray.

BACKGROUND

Aerosol sprays for self-protection are well known. Commercially available self-protection sprays contain a chemical irritant and a propellant. A propellant is a substance which can propel a solution from a container over a sufficient distance for the chemical irritant to reach the target. Self-defense sprays typically have as the active ingredient a lachrymator, such as chloroacetophenone (mace), orthochlorobenzylidenemalononitrile (tear gas), or a pepper extract. Such "pepper sprays" contain an extract of hot pepper and are available with various concentration of capsaicin, which is the primary ingredient producing the effects of pepper spray.

Prior art pepper spray compositions have used hydrocarbons, chlorofluorocarbons, or fluorocarbons as propellants. Most hydrocarbon propellants are flammable, and there are difficulties and potential risks associated with using hydrocarbons as propellants. Chlorofluorocarbons, CFCs, have been used throughout the world in refrigerators, air conditioners, aerosols, and for blowing foam insulation. CFCs are generally viewed as being non-toxic, non-flammable, and safe for use in proximity to humans. Unfortunately, CFCs have a harmful effect on the Earth's ozone layer. Since the ozone layer filters harmful radiation from the Earth's surface, increased incidences of skin cancer are believed to result from reductions in the ozone layer thickness or concentration.

Efforts have been made on an international level to reduce CFC usage. These efforts resulted in the Vienna Convention and the Montreal Protocol, which are designed to protect the ozone layer by limiting the amount of CFCs released into the atmosphere. Since not all CFCs regulated by the protocol pose the same threat to the ozone layer, individual compounds are assigned an ozone depletion potentials (ODP). The ODP is a measure of the possible effect of the chlorine released by a CFC on the ozone concentration in the ozone layer. ODPs are calculated from the atmospheric lifetime of the compound, and from the effectiveness of the chlorine released once the compound is decomposed by ultra-violet light. For example, CFC-11 (otherwise known as F-11, freon-11, arcton, or trichlorofluoromethane) has an ODP of 1.0, as does freon 12 (dichlorodifluoromethane). A compound with an ODP of zero should have no substantial negative impact on the ozone layer.

Hydrofluorocarbons (HFC) have been used to replace CFC compounds in many instances. HFC compounds do not deplete the ozone, but it has recently been discovered that they can have an impact on global warming. Many HFC compounds are more potent warming agents than carbon dioxide. For example, HFC-134a (1,1,1,2-tetrafluoroethane), which has an ODP of zero, has been used as a propellant in aerosols, including pepper spray, but has a high global warming potential (GWP) of 1300.

It is therefore desirable to replace chlorofluorocarbon, flammable hydrocarbon and HFC-134 a propellant used in pepper spray formulations with a non-flammable substitute, which has a low ozone depletion potential, low global warming potential, and addresses some or all of the drawbacks of HFC-134a.

Numerous challenges must be overcome in order to create a successful self-protection pepper spray compositions with a nonflammable, non-ozone depleting propellant. These problems result from the solvent properties of the propellant, as well as difficulties in obtaining a stable, uniform dispersion of the pepper oil.

BRIEF DESCRIPTION

Disclosed herein is a pepper spray composition comprising a chemical irritant and a propellant comprising tetrafluoropropene. The chemical irritant is a pepper extract. Also disclosed is a container comprising the pepper spray composition as well as a method for using the pepper spray composition to repel and/or temporarily incapacitate a target.

The present invention provides a pepper spray composition comprising (a) a chemical irritant that is a pepper-based extract; (b) a propellant, wherein the propellant comprises HFO-1234; and (c) a compatibilizer, wherein the compatibilizer comprises a non-ionic surfactant, and an ionic surfactant. The compatibilizer may further comprise a solvent, preferably an isomer or HCFO-1233, such as trans 1233zd. The pepper-based extract may be oleoresin *capsicum* or another chemical irritant that is sufficient to repel or temporarily incapacitate a target when exposed to the pepper spray composition.

In another embodiment, the present invention provides a pepper spray composition comprising (a) oleoresin *capsicum*; (b) a propellant, wherein the propellant comprises trans HFO-1234ze; (c) polypropylene glycol; (d) a hydrotrop; and (e) a solvent, wherein the solvent comprises trans-1233zd. In some preferred aspects, the polypropylene glycol comprises polypropylene glycol 400; and the hydrotrop is sodium xylene sulfonate.

DETAILED DESCRIPTION

Disclosed herein is a pepper spray composition contained in an aerosol container, which has a propellant that is non-flammable (at ambient temperature and pressure), does not harm the ozone layer, and has a reduced impact on global warming. The pepper spray composition comprises a pepper-based chemical irritant, which is capable of repelling and/or temporarily incapacitating a target, and a propellant comprising tetrafluoropropene. The propellant may have an ozone depletion potential of less than or equal to 0.05 and a global warming potential of less than or equal to 1000, or, more specifically, less than or equal to 750, less than or equal to 500 or, even more specifically, less than or equal to 150.

The pepper spray composition as described herein has a decreased impact on global warming compared to previous aerosol compositions. Additionally, there is no need for a vapor pressure depressant. The pepper spray composition provides a uniform solution/dispersion of the chemical irritant (e.g., oleoresin *capsicum*) and demonstrates excellent stability. Stability of the formulations were tested by putting them in an oven at 40° C. for six weeks. All formulation were found to be stable after thermal treatment.

The propellant comprises hydrofluoro olefin (HFO) 1234. The term "HFO-1234" is used herein to refer to tetrafluoropropenes. Among the tetrafluoropropenes are included 2,3,3,3-tetrafluoropropene (HFO-1234yf) and both cis- and trans-1,3,3,3-tetrafluoropropene (HFO-1234ze). The term HFO-1234ze is used herein to refer to 1,3,3,3-tetrafluoropropene, independent of whether it is the cis- or trans-isomer. The terms "cis HFO-1234ze" and "trans HFO-1234ze" are used herein to describe the cis- and trans-isomers of 1,3,3,3-tetrafluoropropene respectively. The term "HFO-1234ze" therefore includes cis HFO-1234ze, trans HFO-1234ze, and all combinations and mixtures of these. HFO-1234 is commercially available from Honeywell International and is described in U.S. Patent Publication 2008/0292564 which is incorporated by reference herein in its entirety.

The propellant may comprise a single isomer of HFO-1234 (notwithstanding the presence of trace impurities of other HFO-1234 isomers), or a mixture of HFO-1234 isomers.

In a preferred embodiment, the propellant comprises trans-1234ze. In such embodiments, the propellant comprises trans-1234ze in at least about 70% by weight based on the total propellant. In other embodiments, the propellant comprises at least about 75%, 80%, 85%, 90% or 95% by weight based on the propellant. In a further embodiment, the propellant comprises trans-1234ze in at least about 99% by weight based on the total propellant.

The propellant may comprise a mixture of HFO-1234, and particularly trans HFO-1234ze, in combination with one or more additional propellants, e.g., HFO-152a, HFC-134a, HFC-227ea, propane, butane, isobutane, $CO_2$, $N_2$, dimethyl ether, and combinations thereof. An exemplary combination is trans HFO-1234ze and HFC-134a.

The propellant can be present in an amount of about 10 to about 90 weight percent, based on the total weight of the pepper spray composition, and more preferably from about 15 to about 80 weight percent. Within this range the propellant can be present in an amount greater than about 20 weight percent. Also within this range the propellant can be present in an amount less than about 50 weight percent.

The chemical irritant in the compositions is pepper-based agent and includes natural and synthetic oleoresin *capsicum* and capsaicins (including the family of capsaicinoids). Suitable agents include oleoresin *capsicum* and other pepper extracts that contain 8-methyl-N-vanillyl-6-nonenamide (capsaicin) and related compounds.

The active ingredient in the pepper spray is capsaicin, which is a chemical derived from the fruit (peppers) of plants in the *Capsicum* genus. The source of the capsaicin in the pepper spray is preferably oleoresin *capsicum*. The oleoresin *capsicum* the oily or wax-like resin that results from the extraction with organic solvent of capsaicins from the *Capsicum* family of peppers.

The strength of the pepper spray can be adjusted by varying the concentration of the active agent, such as a capsaicin, in the composition. The strength of the pepper spray should be such that it reliably and reproducibly produces the desired effect of repelling and/or temporarily incapacitating a target. For many uses it is also preferred that the pepper spray composition is not so strong that it induces permanent injury or harm to the target or that it requires a lengthy recovery time.

Upon exposure to the pepper spray, the target should exhibit one or more of closing of the eyes, burning sensation on the skin, and shortness of breath. The target may be a human. In other embodiments, the target may be an animal, such as a dog or a bear.

The pepper spray composition can range from about 0.10% to about 10% by weight of capsaicin, and preferably about 0.4% to 5% by weight of capsaicin. Within this range, a concentration of about 0.5% to about 3.0% capsaicin may useful for many self-defense applications.

The pepper oil, such as oleoresin *capsicum*, is not miscible with the HFO-1234 propellant. In order to achieve a uniform, stable dispersion of the pepper oil with the propellant, a compatibilizer composition in used. The compatibilizer composition comprises one or more of a solvent and a surfactant.

The solvent comprises one or more monochlorotrifluoropropene, HCFO-1233, preferably a compound selected from the group consisting of: transCF$_3$CH=CClH (1233zdE, trans-1233zd); cisCF$_3$CH=CClH (1233zdZ, cis-1233zd); transCHF$_2$CF=CClH (1233ydE); cisCHF$_2$CF=CClH (1233ydZ); transCHF$_2$CH=CClF (1233zbE); cisCHF$_2$CH=CClF (1233zbZ); transCHF$_2$CCl=CHF (1233xeE); cisCHF$_2$CCl=CHF (1233xeZ); CH$_2$FCCl=CF$_2$ (1233xc); transCHFClCF=CFH (1233yeE); cisCHFClCF=CFH (1233yeZ); CH$_2$ClCF=CF$_2$ (1233yc); CF$_2$ClCF=CH$_2$ (1233xf); and combinations of two or more of these. In preferred embodiments the monochlorotrifluoropropene is 1233zd, and particularly trans-1233zd. Other solvents may include trans-dichloroethylene, and the like.

Other solvents or co-solvents may include alcohols, glycols including glycol ethers, ethoxylated glycols, and mixtures thereof. Alcohols include ethanol, propanol, iso-propanol, glycerin, propanediol, 1-propoxy-2-propanol, 1-butoxy-2-propanol, and the like, and mixtures thereof. Glycols include dipropylene glycol n-butyl ether, dipropylene glycol n-propyl ether, diethylene glycol butyl ether, dipropylene glycol monomethyl ether, ethylene glycol monopropyl ether, diethylene glycol monomethyl ether, diethylene glycol monoethyl ether, triethyleneglycol monobutyl ether, propylene glycol monomethyl ether, triethylene glycol monomethyl ether, tripropylene glycol monobutyl ether, and the like.

The solvent, and particularly trans-1233zd, if present in the pepper spray composition, may be present in an amount from about 5% to about 50% by weight of the pepper spray composition. In some embodiments, the solvent is present in an amount from about 10% to about 40% by weight of the pepper spray composition.

The surfactant may be a non-ionic surfactant, an ionic surfactant, or a mixture thereof. Non-ionic surfactants for use in the pepper spray composition include polyethers, glycol ethers and ethoxylated alcohols, and mixtures thereof. Polyethers, such as polyethylene glycol, polypropylene glycol, and mixtures thereof, are preferred. In some embodiments, the non-ionic surfactant comprises polypropylene glycol. Ethoxylated alcohols may include lutensol, bio-soft, sasol, and Guerbet alcohol sulfate. Glycol ethers may include Dowanol DPM, DPnB, etc.

The polyether, such as polypropylene glycol, preferable has a molecular weight under about 2000, and more preferably under about 1000. In preferred embodiments, the non-ionic surfactant comprises polypropylene glycol 400.

The non-ionic surfactant, and particularly polypropylene glycol may be present in an amount from about 10% to about 50% by weight of the pepper spray composition. In some embodiments, the non-ionic surfactant is present in an amount from about 20% to about 40% by weight of the pepper spray composition.

Ionic surfactants for use in the pepper spray composition include hydrotrops. Hydrotrops consists generally of two parts, an anionic group such as carboxylate or sulfonate, and a hydrophobic aromatic ring or ring system. Preferred hydrotrops include salts of xylene sulfonate, para-toluene sulfonate, cumene sulfonate, and the like. The salts may comprise sodium, potassium, ammonium, or the like. A particularly preferred hydrotrop for use in the pepper spray is sodium xylene sulfonate.

The ionic surfactant, and particularly hydrotrops such as sodium xylene sulfonate may be present in an amount from about 5% to about 40% by weight of the pepper spray composition. In some embodiments, the ionic surfactant is present in an amount from about 10% to about 20% by weight of the pepper spray composition.

The pepper spray compositions may also contain, surfactants, rheology modifiers, dyes (either visible or UV-reactive), and anesthetic chemicals. Anesthetic chemicals can be chloroform, cyclopropane, desflurane, enflurane, halothane, methoxyflurane, ethylene, ethyl ether, isoflurane, sevoflurane, trichloethylene, xenon, etc.

The pepper spray composition according to the present invention is typically supplied in canisters, which are often small enough to be carried in a pocket or purse. Pepper spray can also be purchased concealed in items such as rings. There are also pepper spray projectiles available, which can be fired from a paintball gun.

EXAMPLES

Comparative Example 1

An active irritant composition consisting of oleo-*capsicum* resin (85%), oleic acid mono ester with glycerin (5.0%), and Sun flower oil (10.0%) was prepared and used as the chemical irritant formulation for these examples. Several compositions were prepared in order to test the compatibility for the preparation of a uniform dispersion of this active irritant in trans-1234ze, trans1233zd, and in various mixtures of trans-1234ze and trans-1233zd.

The mixing for these experiments were done in a Fisher-Porter glass tube capable of handling high pressure up to 120 psi. Initially the active irritant composition (indicated as PO for Pepper Oil) was added to the tube, together with other ingredients other room temperature liquid components if present, and then a refrigerated sample of trans1233zd, when used in the formulation, was added to it. When trans1234ze was present, it was added through a glass burette using a pressure device. Vapor pressure in the tube was measured using a pressure gauge mounting to the tube. Average pressure in the tube was about 55 psi.

The formulations tested are identified in Table CE1 below, and in each case the indicated amount of active irritant composition (indicated in the table below as PO for Pepper Oil) is mixed with indicated amount of trans1234ze and in one case a mixture of trans1233zd and trans1234zd and/or additional components, and in each case instability and/or separation of components is noted.

TABLE-CE1

(Dispersion of pepper Oil)

| Example | Formulation Composition | Remarks |
| --- | --- | --- |
| CE1. | 1.0 g PO + 6.47 g trans1234ze | The mixture was not stable and separated into two phases. The lower portion was 1234ze propellant. |
| CE2 | 1.2 g PO + 1 g emulsifier (Mesodol 1-3) and 7.49 g trans1234ze | Mixture was not stable |
| CE3 | 0.5 g. PO + 0.5 g of Polyethylene glycol-400 + 4.86 g. trans1234ze | Two phases were formed |
| CE4 | 0.5 g. pepper oil + 0.51 g. PEG-400 + 1.0 g. Sodium xylene sulfonate + 6.7 g. trans1234ze | Mixture was not stable |
| CE5 | 0.51 g. pepper oil + 5.21 g. 1233zd + 5.20 g. 1234ze | Mixture was not stable and separated into two phases |
| CE6 | 2.06 g. Propylene glycol-P400 + 1.02 g. sodium xylene sulfonate + 1.01 g. pepper oil + 8.72 g. 1234ze | Mixture was not stable and separated into two phases |
| CE7 | 2.06 g. Propylene glycol-P400 + 1.02 g. sodium xylene sulfonate + 1.01 g. pepper oil + 7.76 g. 1234ze | Mixture was not stable and separated into two phases |
| CE8 | 2.06 g. Propylene glycol-P400 + 1.02 g. sodium xylene sulfonate + 1.01 g. pepper oil + 6.54 g. 1234ze | Mixture was not stable and separated into two phases |
| CE9 | 2.06 g. Propylene glycol-P400 + 1.02 g. sodium xylene sulfonate + 1.01 g. pepper oil + 4.86 g. 1234ze | Mixture was not stable and separated into two phases |
| CE10 | 2.06 g. Propylene glycol-P400 + 1.02 g. sodium xylene sulfonate + 1.01 g. pepper oil + 3.88 g. 1234ze | Mixture was not stable and separated into two phases |
| CE11 | 2.06 g. Propylene glycol-P400 + 1.02 g. sodium xylene sulfonate + 1.01 g. pepper oil + 3.88 g. 1234ze | Mixture was not stable and separated into two phases |

Example 1. Solubilization of Pepper Oil in 1234ze, 1233zd, and in Mixtures of 1234ze and 1233zd The same active irritant composition as used in Comparative Example 1 was prepared and used as the chemical irritant formulation for these examples. Several compositions were prepared in order to test the compatibility for the preparation of a uniform dispersion of this active irritant in trans-1234ze, trans-1233zd, and in various mixtures of trans-1234ze and trans-1233zd. The formulations tested are identified in Table 1 below, and in each case the indicated amount of active irritant composition (indicated in the table below as PO for Pepper Oil) is mixed with indicated amount of trans1234ze and/or trans1233zd and/or additional components. In each case the result observed is noted in the remarks column of Table E1 below:

TABLE-E1

(Dispersion of pepper Oil)

| Experiment # | Formulation Composition | Remarks |
|---|---|---|
| 1A | 1.6 g PO + 2.85 g trans1233zd | One Phase |
| 1B | 0.52 g PO + 5.31 g trans1233zd | One Phase |
| 2 | 1.2 g PO + 1.04 g water + 2.2 g 1233zd | One phase |
| 3 | 5.0 g pepper oil, 30.0 g H2O, 55.0 g 1233zd, 10.0 g 1234ze, 80 psig CO2 | One Phase |
| 4 | 1.0 g pepper oil, 79.0 g 1233zd, 20.0 g 1234ze, 80 psig CO2 | One Phase |
| 5 | 2.51 g. polypropylene glycol (P-400) + 0.42 g. pepper oil + 1.25 g. sodium xylene sulfonate + 4.56 g. 1234ze | One Phase |
| 6 | 2.06 g. Propylene glycol-P400 + 1.02 g. sodium xylene sulfonate + 1.01 g. pepper oil + 3.25 g. 1234ze | One Phase |
| 7 | 1.53 g. Pepper oil + 1.55 g. sodium xylene sulfonate + 3.01 g. Propylene glycol (P-400) + 4.52 g. 1233zd + 2.51 g. 1234ze | Dispersed and stable |
| 8 | 1.62 g. Pepper oil + 1.61 g. sodium xylene sulfonate + 3.05 g. Propylene glycol (P-400) + 1.14 g. 1233zd + 4.18 g. 1234ze | Dispersed and stable |
| 9 | 1.53 g. Pepper oil + 1.52 g. sodium xylene sulfonate + 3.01 g. Propylene glycol (P-400) + 3.41 g. 1234ze | Dispersed and stable |
| 10 | 1.52 g. Pepper oil + 1.52 g. sodium xylene sulfonate + 3.03 g. Propylene glycol (P-400) + 3.02 g. 1233zd + 1.01 g. 1234ze | Dispersed and stable |

The invention claimed is:

1. A pepper spray composition comprising:
    (a) from about 1% to about 20% by weight of a chemical irritant comprising as an active component a pepper-based extract;
    (b) from about 10% to about 80% by weight of a propellant, wherein the propellant comprises at least about 70% by weight of transHFO-1234ze;
    (c) at least about 5 percent of a solvent, wherein said solvent comprises transHFO-1233zd; and
    (d) from about 10% to about 50% by of a non-ionic surfactant, wherein said % by weight of said (a), (b) (c) and (d) are based on the total weight of said components (a)-(d) in the pepper spray composition.

2. The pepper spray composition of claim 1 wherein said solvent consists essentially of transHFO-1233zd.

3. The pepper spray composition of claim 2, wherein the solvent consists of transHFO-1233zd.

4. The pepper spray composition of claim 1, wherein the pepper-based extract is oleoresin *capsicum*.

5. The pepper spray composition of claim 1, wherein the propellant comprises at least about 80% by weight of trans-HFO 1234ze.

6. The pepper spray composition of claim 1, wherein the propellant comprises at least about 90% by weight of trans-HFO 1234ze.

7. The pepper spray composition of claim 1, wherein the propellant comprises at least about 99% by weight of trans-HFO 1234ze.

8. The pepper spray composition of claim 1, wherein said non-ionic surfactant is a polyether.

9. The pepper spray composition of claim 8, wherein the polyether is polypropylene glycol.

10. The pepper spray composition of claim 9 further comprising an ionic surfactant and wherein said ionic surfactant is a hydrotrop.

11. The pepper spray composition of claim 10, wherein the ionic surfactant is sodium xylene sulfonate.

12. A pepper spray composition comprising:
    (a) from about 1% to about 20% by weight of a chemical irritant comprising as an active component a pepper-based extract;
    (b) from about 10% to about 80% by weight of a propellant, wherein the propellant comprises at least about 70% by weight of transHFO-1234ze;
    (c) at least about 5 percent of a solvent, wherein said solvent comprises transHFO-1233zd; and
    (d) from about 10% to about 50% by of an ionic surfactant, wherein said % by weight of said (a), (b) (c) and (d) are based on the total weight of said components (a)-(d) in the pepper spray composition.

13. The pepper spray composition of claim 12 wherein said solvent consists essentially of transHFO-1233zd.

14. The pepper spray composition of claim 12, wherein the solvent consists of transHFO-1233zd.

15. The pepper spray composition of claim 12, wherein the pepper-based extract is oleoresin *capsicum*.

16. The pepper spray composition of claim 15, wherein the propellant comprises at least about 80% by weight of trans-HFO 1234ze.

17. The pepper spray composition of claim 15, wherein the propellant comprises at least about 90% by weight of trans-HFO 1234ze.

18. The pepper spray composition of claim 15, wherein the propellant comprises at least about 99% by weight of trans-HFO 1234ze.

19. The pepper spray composition of claim 11, wherein said ionic surfactant is a hydrotrop.

20. The pepper spray composition of claim 19 further comprising a non-ionic surfactant.

21. The pepper spray composition of claim 19, wherein the ionic surfactant is sodium xylene sulfonate.

22. A pepper spray composition comprising:
    (a) oleoresin *capsicum;*
    (b) a propellant, wherein the propellant comprises trans HFO-1234ze;
    (c) polypropylene glycol;
    (d) a hydrotrop; and
    (e) a solvent, wherein the solvent comprises trans-1233zd.

23. The pepper spray composition of claim 22, wherein the polypropylene glycol comprises polypropylene glycol 400; and the hydrotrop is sodium xylene sulfonate.

* * * * *